United States Patent [19]

Katz

[11] Patent Number: 4,560,239

[45] Date of Patent: Dec. 24, 1985

[54] LIQUID CRYSTAL ACTIVE LIGHT SHIELD

[76] Inventor: Amnon Katz, 401 Forrest Hill La., Grand Prairie, Tex. 75051

[21] Appl. No.: 584,772

[22] Filed: Feb. 29, 1984

[51] Int. Cl.⁴ .............................................. G02F 1/13
[52] U.S. Cl. ............................................... 350/331 R
[58] Field of Search ................................... 350/331 R

[56] References Cited

U.S. PATENT DOCUMENTS

| 4,155,122 | 5/1979 | Budmiger | 350/331 R X |
| 4,456,335 | 6/1984 | Mumford | 350/331 R |
| 4,462,661 | 7/1984 | Witt | 350/331 R |

Primary Examiner—John K. Corbin
Assistant Examiner—Richard Gallivan

[57] ABSTRACT

A device for protection against light of high and rapidly varying intensity which automatically and electronically maintains a constant intensity of transmitted light.

2 Claims, 2 Drawing Figures

LIQUID CRYSTAL ACTIVE LIGHT SHIELD

BACKGROUND

This invention relates to eye protection devices such as sunglasses, windows, and windshields. Light absorbing eyewear and panels are in common use. Some of these automatically adjust their absorption properties to the level of ambient light. Such adjustment in the devices currently in use is achieved by a reversible photo-chemical or photo-physical process, which requires many seconds before the adjustment is effective. This slow response is inadequate for many applications. The present invention is a device that achieves the adjustment of the degree of light absorption in a matter of miliseconds. The effect of changes in light level is neutralised before the changes are noticed and before they have any detrimental effect. This invention offers effective eye protection in situations of rapidly changing light intensity such as are encountered when driving in and out of tunnels, flying in and out of cloud, and near lightning or nuclear explosion.

SUMMARY

The present invention teaches how to automatically and continuously limit the intensity of light transmitted by a transparent panel to a desired level independently of the intensity of impinging light by use of a thin transparent active light shield disposed in series with the panel.

The active light shield of this invention is comprised of a layer of liquid crystal contained between two transparent electrodes and between two plane polarizes and of an electronic device that governs the voltage between the electrodes. The electronic device includes a photocell and derives the voltage applied to the electrodes from the signal produced by said photocell.

Light penetrating the active light shield is polarized by the first polarizer. The plane of polarization is rotated as the light passes the liquid crystal layer. The second polarizer is so aligned relative to the first, that in the absence of voltage across the electrodes, its plane of polarization is the same as that of the light reaching it through the shield. Thus with no signal to the electrodes, the shield is transparent. When a voltage is applied across the electrodes, the amount of rotation of the plane of polarization of light passing the liquid crystal layer is altered. This causes the light arriving at the second polarizer to be plane polarized at an angle to the plane of polarization of said polarizer. This results in the coefficient of light transmission of the shield to be reduced in proportion to the square of the cosine of such angle.

The signal to the electrodes is derived from the photocell and devised so as to decrease the transmission coefficient of the shield in proportion to the intensity of light incident on it. The intensity of the light transmitted is thus kept at or below a constant predetermined level.

The preferred method of generating the appropriate signal is to position the photocell behind the shield, so that the light measured is only that which is transmitted. The signal from the photocell is then compared with a constant reference level, and the difference used as a negative feedback to maintain a constant intensity of transmitted light. The resultant intensity is adjustable by adjusting the reference signal. This arrangement enjoys the further advantage that the photocell is itself protected from the effects of the unregulated incident light.

PREFERRED EMBODIMENT

A preferred embodiment of the active light shield is described in the following and shown in the drawings. In the preferred embodiment the liquid crystal layer and transparent electrodes form a twisted nematic cell and are disposed between plane polarizers crossed at right angle as described in reference 1. The photocell is a phototransistor. The voltage applied to the electrodes is an alternating square wave.

BRIEF DISCUSSION OF THE DRAWINGS

Figure 1:
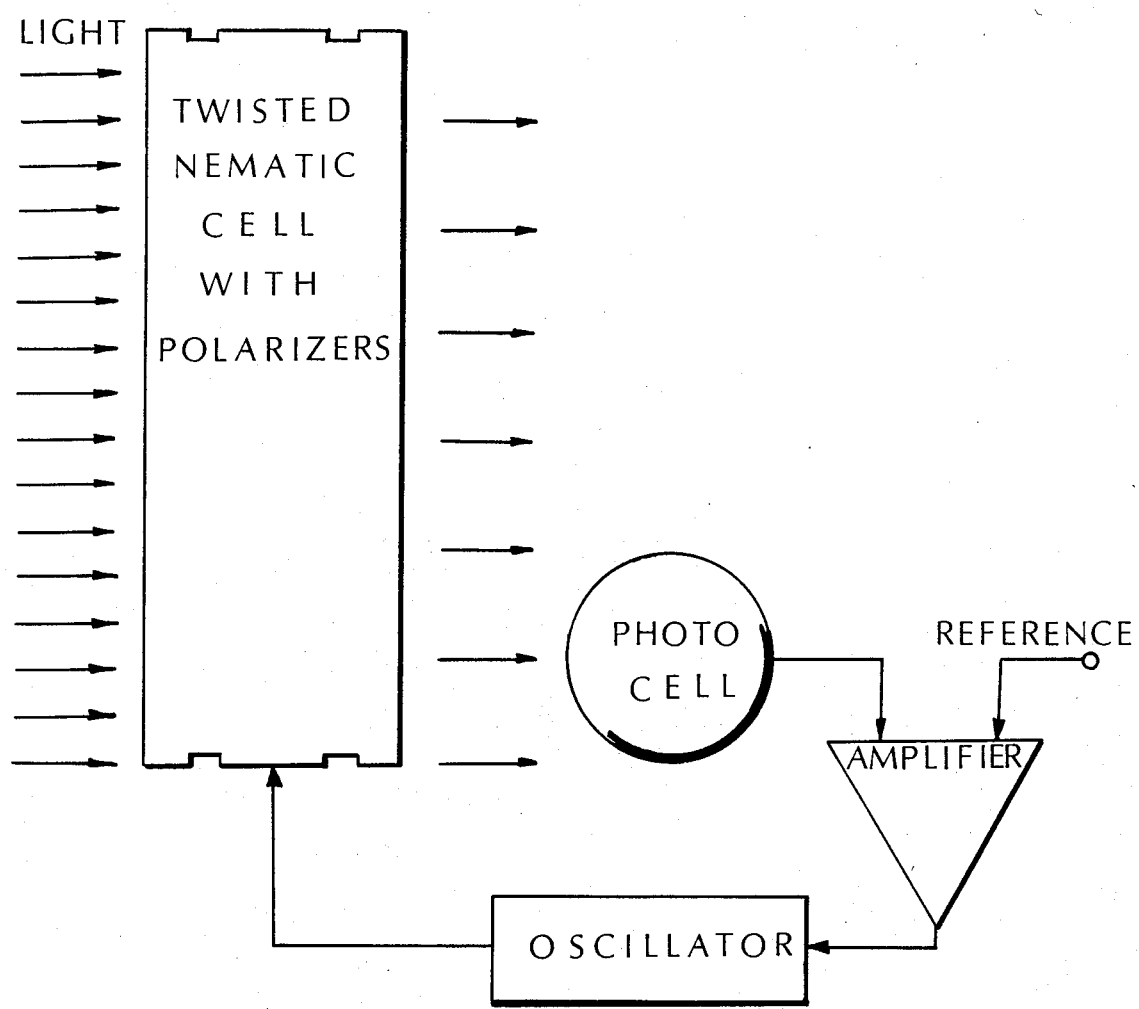
FIG. 1 is a block diagram showing the major assemblies of the preferred embodiment and their functional relationships.
Figure 2:
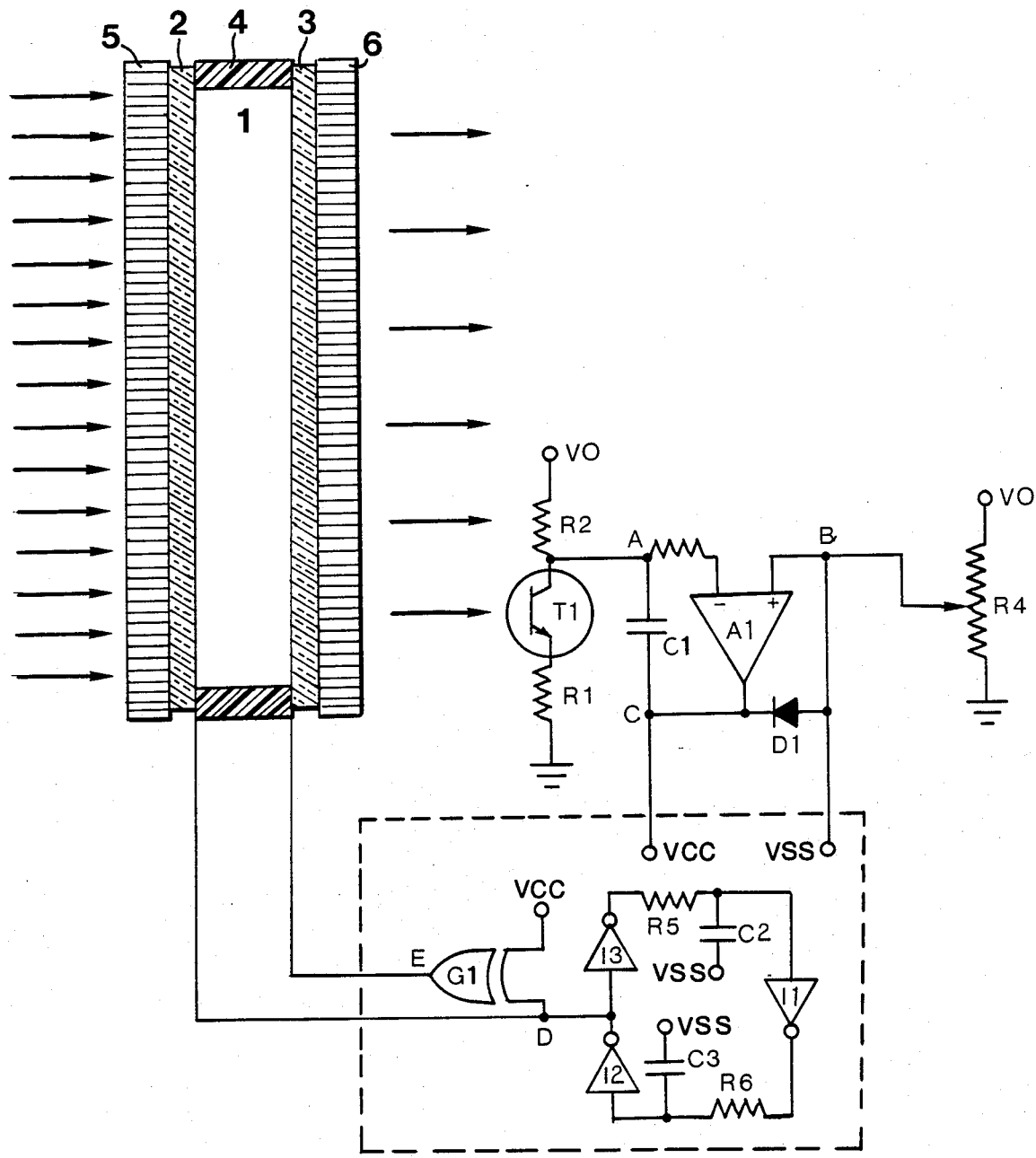
FIG. 2 is a schematic showing the details of the active light shield including the electronics.

The major components detailed in FIG. 2 are:
1—Liquid crystal layer.
2,3—Glass plates with layer of $SnO_2$ deposited on inside to form electrodes.
4—Seal.
5,6—Plane polarizers (crossed orientations).
T1—Phototransistor.
A1—Operational amplifier.
R4—Potentiometer.
I1,I2,I3—Logical inverters.
G1—Exclusive-or gate.

DETAILED DESCRIPTION OF THE PREFERRED EMBODIMENT

The layer of liquid crystal 1 is of the nematic variety and is contained between glass plates 2 and 3, and secured by seal 4. A thin layer of $SnO_2$ is deposited on the inside of the glass to form transparent electrodes. The liquid crystal layer and its container form a twisted nematic cell as described in reference 1. The twist of the preferred direction of the liquid crystal between electrodes is ninety degrees. See reference 1 for further details and properties of this arrangement.

The twisted nematic cell is disposed between plane polarizers 5 and 6 whose planes of polarization are crossed at right angle. With no voltage applied to the electrodes, the coefficient of transmission of the shield attains its maximum value of approximately one half. A field applied to the electrodes can reduce the coefficient of transmission continuously all the way to zero (reference 1).

The signal applied to the electrodes is a square wave generated by an oscillator comprised of the CMOS logical inverters I1,I2,I3, and of the resistors R5, R6 and capacitors C2, C3. The resistors and capacitors determine the frequency and duty cycle of the wave. The wave amplitude is between the supply voltages VCC and VSS. This signal is present between points C and D. The logical exclusive-or gate G1 transforms it into a wave between voltage levels $+(VCC-VSS)$ and $-(VCC-VSS)$ between points D and E. This last signal, which has no DC component is applied to the electrodes on plates 2,3.

The photocell employed in the preferred embodiment is a phototransistor T1 connected in series between resistors R1 and R2 and between the positive supply voltage V0 on one side and ground on the other. The phototransistor is situated behind the light shield so that it is exposed to the transmitted light. The voltage at point A is used as the indicator of the measured light intensity. This voltage varies from V0 when the transistor does not conduct (no light measured) to V0.R2/(R1+R2) for a saturated light measurement.

The signal produced by the phototransistor T1 at point A is compared to a reference level produced at point B by the reference potentiometer R4. The operational amplifier A1 integrates the voltage difference between points A and B and produces at point C a signal given by $$VC = -\int (VA - VB) dt /(R3C1).$$

This voltage is used as the supply voltage VCC for the oscillator. The reference voltage is used as VSS.

In a steady state the signal VA−AB must vanish. This implies that the voltage VC is such as to maintain the light intensity behind the shield at the level that causes the voltage at A to match the reference voltage at B. The reference level, and with it the light intensity behind the shield, can be varied by use of the potentiometer R4.

If the steady state should be disturbed, a train of events is set in motion to restore VA to VB. If the intensity of incident light should increase, the resistance of the phototransistor T1 is reduced, causing a reduction in VA. The deviation VA−VB becomes negative, leading to an increase in the voltage VC, and in turn an increase in the amplitude of the signal applied to the electrodes and a reduction in the light transmission coefficient of the shield. The changes in VC and the light transmission coefficient continue until VA is brought back up to VB.

Conversely, should the intensity of incident light decrease, then VA rises, VC drops, and the light transmission coefficient of the shield increases. These changes continue until either the light intensity behind the shield is brought back up to the reference level (VA=VB), or VC drops below VB. In this last case, the voltage at points B and C is equalized through the diode D1, no power is applied to the oscillator, and no signal to the electrodes, and the shield's coefficient of light transmission is at its maximum value. This situation prevails when the intensity of incident light is insufficient to maintain the intensity of transmitted light behind the shield at the reference level.

The response time of the voltage VC to changes in VA is of the order of R3.C1 which can be kept in the microsecond range. The response times of all other electronic components are well below a microsecond. This leaves the liquid crystal in the twisted nematic cell as the slowest part of the system. The response time of the cell is typically of the order of 10 miliseconds for blocking excess light and of the order of 100 miliseconds for readmitting light. These times dominate all others and are therefore representative of the response time of the active light shield as a whole.

REFERENCES

1. Schadt and Helfrich, Appl. Phys. Lett. 18, 127 (1971).

I claim:

1. In protective eyewear or transparent light shielding subject to varying intensity of incident light, apparatus comprising the combination of
   a layer of liquid crystal contained between two transparent electrodes and between two plane polarizers,
   a photocell which is placed behind said eyewear or shielding and measures only transmitted light, electronic circuitry to process the output of such photocell and produce a signal into said electrodes so as to reduce the transmission coefficient of lght through the combination of said polarziers and liquid crystal in proportion to the intensity of light incident thereon, and wherein the deviation of the signal produced by the photocell from a reference level is used as a negative feedback to maintain a constant intensity of transmitted light."

2. Apparatus in accordance with claim 1 where the reference level is adjustable by the user.

* * * * *